(12) United States Patent
Detweiler et al.

(10) Patent No.: US 11,672,580 B2
(45) Date of Patent: Jun. 13, 2023

(54) DRIVEN UNIVERSAL SCREW GUIDE

(71) Applicant: Jace Medical, LLC, Warsaw, IN (US)

(72) Inventors: Jason F. Detweiler, Warsaw, IN (US); Scott Steffensmeier, Winona Lake, IN (US)

(73) Assignee: Jace Medical, LLC, Warsaw, IN (US)

( * ) Notice: Subject to any disclaimer, the term of this patent is extended or adjusted under 35 U.S.C. 154(b) by 0 days.

(21) Appl. No.: 17/882,187

(22) Filed: Aug. 5, 2022

(65) Prior Publication Data

US 2022/0370105 A1 Nov. 24, 2022

Related U.S. Application Data

(63) Continuation of application No. 17/117,604, filed on Dec. 10, 2020, now Pat. No. 11,446,068.

(60) Provisional application No. 62/947,570, filed on Dec. 13, 2019.

(51) Int. Cl.
*A61B 17/88* (2006.01)
*A61B 17/80* (2006.01)
*A61B 17/90* (2006.01)

(52) U.S. Cl.
CPC ........ *A61B 17/8875* (2013.01); *A61B 17/808* (2013.01); *A61B 17/8085* (2013.01); *A61B 17/8894* (2013.01); *A61B 17/90* (2021.08)

(58) Field of Classification Search
CPC ..... A61B 17/808; A61B 17/865; A61B 17/88; A61B 17/8872; A61B 17/8875; A61B 17/888; A61B 17/8886; A61B 17/8888; A61B 17/8891; A61B 17/8894; A61B 17/90; B25B 17/00; B25B 17/02
See application file for complete search history.

(56) References Cited

U.S. PATENT DOCUMENTS

| | | | |
|---|---|---|---|
| 1,307,193 | A | 6/1919 | Firster |
| 4,140,161 | A | 2/1979 | Russo et al. |
| 5,190,545 | A | 3/1993 | Corsi et al. |
| 6,007,538 | A | 12/1999 | Levin |
| 6,012,359 | A | 1/2000 | Lin |
| 6,244,141 | B1 | 6/2001 | Han |
| 7,588,576 | B2 | 9/2009 | Teague et al. |
| 8,414,594 | B2 | 4/2013 | Berger et al. |
| 10,159,503 | B2 * | 12/2018 | Niederberger ..... A61B 17/1728 |

(Continued)

FOREIGN PATENT DOCUMENTS

JP 3106821 B2 11/2004

OTHER PUBLICATIONS

"U.S. Appl. No. 17/117,604, Non Final Office Action dated Dec. 6, 2021", 13 pgs.

(Continued)

*Primary Examiner* — Larry E Waggle, Jr.
(74) *Attorney, Agent, or Firm* — Schwegman Lundberg & Woessner, P.A.

(57) ABSTRACT

A driven fastener guide for guiding a fastener into a hole of a bone plate. The driven fastener guide includes an elongated driver configured for connecting to a drill and a fastener guide member operably connected to the elongated driver. The fastener guide member includes a split body and a through-bore configured for receiving the fastener. The fastener guide member is configured for aligning the fastener relative to the hole of the bone plate.

20 Claims, 14 Drawing Sheets

(56) References Cited

U.S. PATENT DOCUMENTS

| | | |
|---|---|---|
| 10,758,290 B2 | 9/2020 | Detweiler et al. |
| 10,772,666 B2 | 9/2020 | Johnston, Jr. et al. |
| 2010/0274249 A1 | 10/2010 | Dell Oca |
| 2018/0177510 A1 | 6/2018 | Whitaker et al. |
| 2021/0113255 A1 | 4/2021 | Stockdill et al. |
| 2021/0177472 A1 | 6/2021 | Detweiler et al. |

OTHER PUBLICATIONS

"U.S. Appl. No. 17/117,604, Notice of Allowance dated May 16, 2022", 5 pgs.

"U.S. Appl. No. 17/117,604, Response filed May 3, 2022 to Non Final Office Action dated Dec. 6, 2021", 10 pgs.

* cited by examiner

DRIVEN UNIVERSAL SCREW GUIDE

CROSS REFERENCE TO RELATED APPLICATIONS

This is a non-provisional application based upon U.S. provisional patent application Ser. No. 62/947,570, entitled "DRIVEN UNIVERSAL SCREW GUIDE", filed Dec. 13, 2019, which is incorporated herein by reference.

BACKGROUND OF THE INVENTION

1. Field of the Invention

The present invention relates generally to bone closure devices for securing bone portions together, and more particularly, to a driven screw guide for use with a bone plate.

2. Description of the Related Art

Some surgical procedures involve separating a bone into portions and reuniting the bone portions after conducting the desired operation within the body. Various devices are used to refix or resecure the bone portions to one another. For example, in a sternal reapproximation medical procedure, one or more sternal fixation or closure devices can be used to hold and secure the portions of the sternum together. Generally, each sternal fixation device will engage or otherwise wrap around the sternal portions in order to hold and secure the sternal portions together. One such fixation device is a bone plate with one or more threaded holes for receiving bone screws therein. The bone plate spans across the bone portions, and upon screwing the bone screws into the bone portions, the bone plate holds the bone portions together.

A positioning device or screw guide may be used in conjunction with a bone plate to help guide the bone screw into the bone plate. A typical screw guide includes a screw cartridge with multiple screws therein and a tubular body with a channel or through-bore. The channel of the screw guide receives the screw, from the cartridge, and guides the bone screw to the desired threaded hole in the bone plate. The screw guide may also guide the screwdriver or drill bit which screws the bone screw into the threaded hole of the bone plate.

What is needed in the art is a screw guide multitool for collectively retaining, guiding, and driving a screw into a bone plate.

SUMMARY OF THE INVENTION

The present invention provides a multitool in the form of a driven fastener guide that collectively retains a fastener therein, secures itself relative to a bone plate, aligns the fastener to the desired hole of the bone plate, and drives the fastener into the bone plate. The driven fastener guide includes an elongated driver configured for connecting to a drill and a fastener guide member operably connected to the elongated driver. The fastener guide member includes a split body and a through-bore configured for receiving the fastener. The fastener guide member is configured for aligning the fastener relative to the hole of the bone plate.

The invention in one form is directed to a driven fastener guide for guiding a fastener into a hole of a bone plate. The driven fastener guide includes an elongated driver configured for connecting to a drill and a fastener guide member operably connected to the elongated driver. The fastener guide member includes a split body and a through-bore configured for receiving the fastener. The fastener guide member is configured for aligning the fastener relative to the hole of the bone plate.

The invention in another form is directed to a method for securing bone portions of an individual. The method includes an initial step of providing a driven fastener guide. The driven fastener guide is configured for guiding a fastener into a hole of a bone plate. The driven fastener guide includes an elongated driver configured for connecting to a drill and a fastener guide member operably connected to the elongated driver. The fastener guide member includes a split body and a through-bore configured for receiving the fastener. The method further includes inserting the fastener into the through-bore of the split body. The method further includes aligning the fastener relative to the hole of the bone plate by screwing the fastener guide member into the hole of the bone plate. The method further includes simultaneously unscrewing the fastener guide member from the hole of the bone plate and screwing the fastener into the hole of the bone plate.

An advantage of the present invention is that the driven fastener guide collectively retains, aligns, and inserts the fastener into the desired hole of the bone plate.

Another advantage of the present invention is that the driven fastener guide simultaneously unscrews the fastener guide member and inserts the fastener within the hole of the bone plate so that the fastener does not become misaligned.

BRIEF DESCRIPTION OF THE DRAWINGS

The above-mentioned and other features and advantages of this invention, and the manner of attaining them, will become more apparent and the invention will be better understood by reference to the following description of embodiments of the invention taken in conjunction with the accompanying drawings, wherein.

Corresponding reference characters indicate corresponding parts throughout the several views. The exemplifications set out herein illustrate embodiments of the invention and such exemplifications are not to be construed as limiting the scope of the invention in any manner.

DETAILED DESCRIPTION OF THE INVENTION

Figure 5:
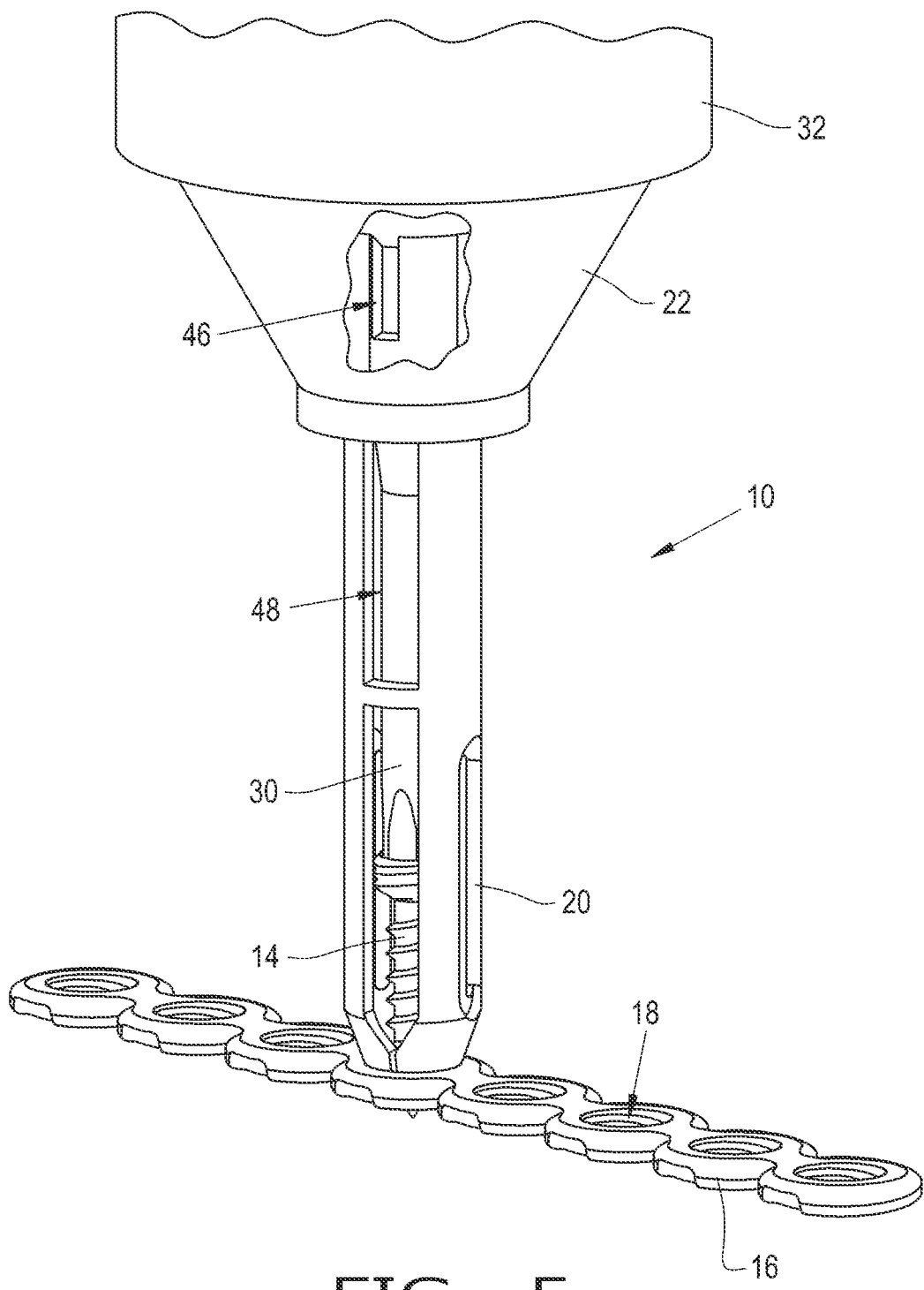
FIG. 5 is a perspective view of the end of the screw guide driver of FIG. 1, wherein the screw guide driver is shown to be attached to the bone plate and the screw is positioned within the screw guide.
Figure 6:
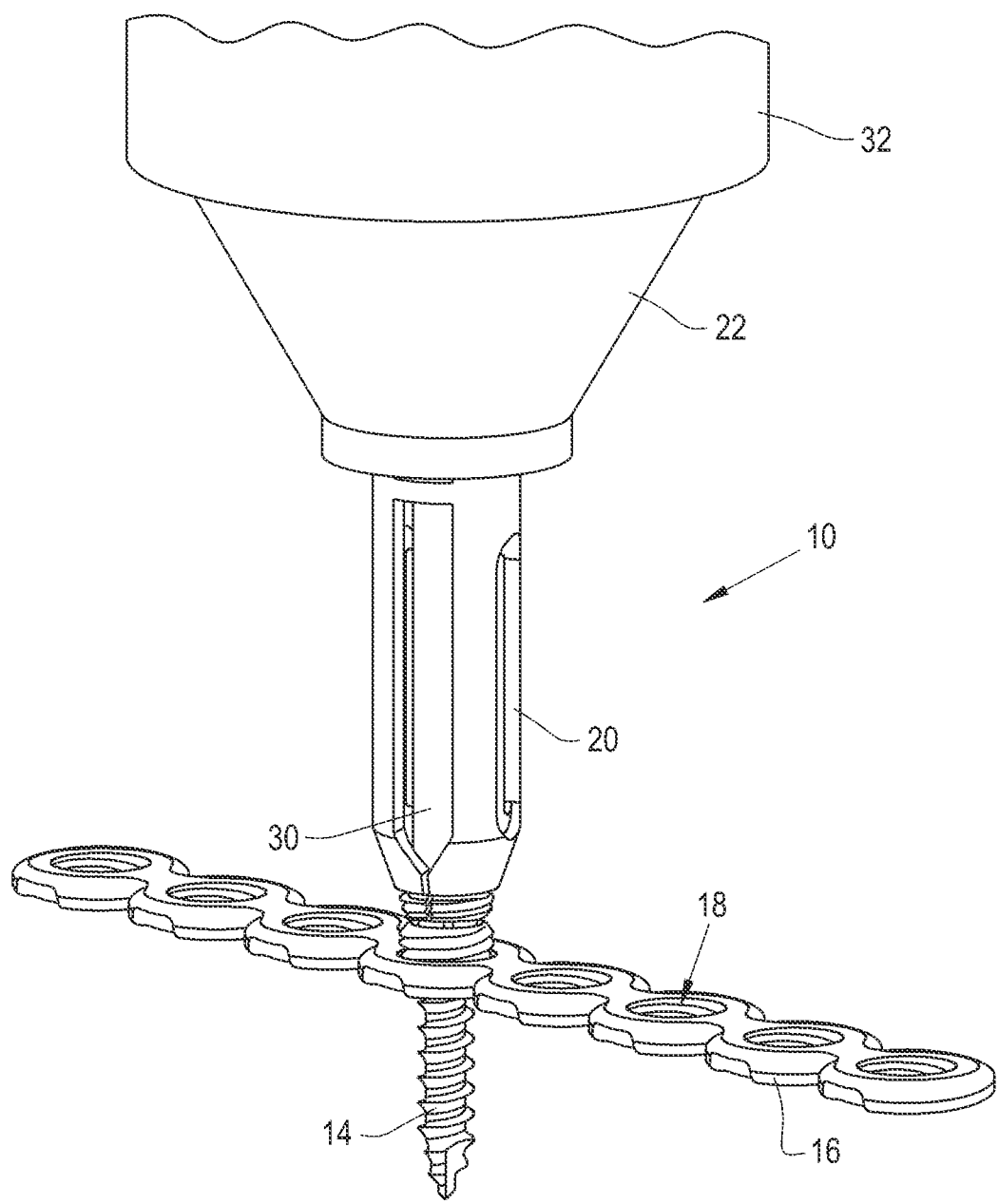
FIG. 6 is a perspective view of the end of the screw guide driver of FIG. 1, wherein the screw guide driver is shown to be attached to the bone plate and the screw is seated within the bone plate.
Figure 7:
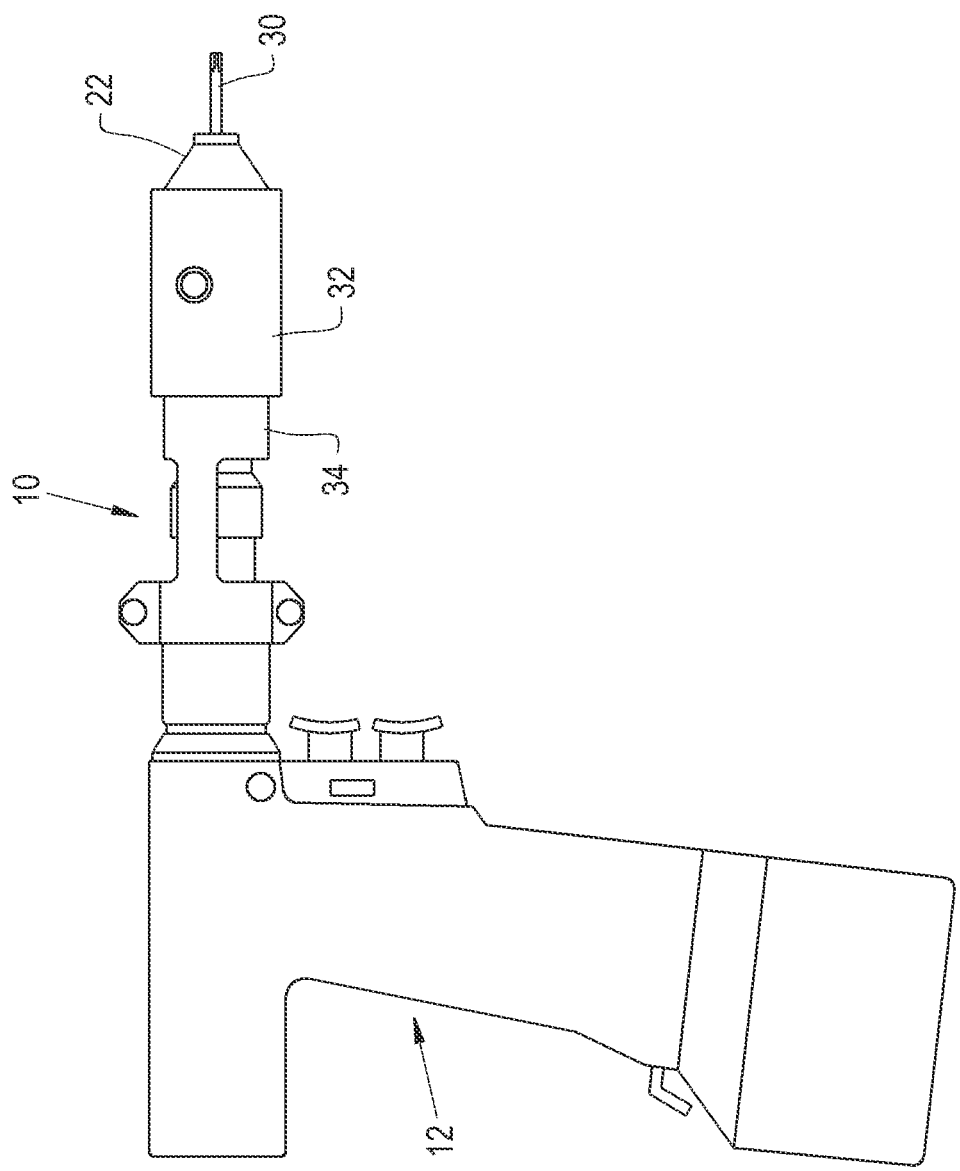
FIG. 7 is a side view of a drill with the screw guide driver of FIGS. 1-6 attached thereto.

Referring now to the drawings, and more particularly to FIGS. 1-7, there is shown a driven fastener guide 10 which is driven by a handheld driver, such as an electric drill 12 (FIG. 7). The driven fastener guide 10 is capable of collectively holding, guiding, and inserting fasteners 14 into variously configured fixation devices 16, such as bone plates 16. The driven fastener guide 10 is also capable of removing and holding fasteners 14 therein. In operation, the driven fastener guide 10 may removably engage with the bone plate 16 for easily guiding the fastener 14 into or out of the bone plate 16. The fastener 14 may be in the form of a bone screw 14. Alternatively, the fastener 14 may be in the form of a marking device, a peg, a headless pin, etc.

Alternatively to being driven by an electric drill 12, the driven fastener guide 10 may be manually driven. For instance, the driven fastener guide 10 may connect to a handle portion for allowing a user to manually rotate the driven fastener guide 10. The driven fastener guide 10 may comprise any desired material, such as metal and/or plastic. Thereby, the drill 12 may be in the form of any desired electric and/or manually operated drill 12.

The driven fastener guide 10 generally includes a deformable stem or fastener guide member 20, a stem mounting member 22 which may be in the form of a collar 22, a gearing assembly including a gear mount 24 which mounts multiple gears 26, 28 thereon, an elongated driver 30 operably connected to the gears 26, 28, and a housing or casing 32. After inserting a fastener 14 into the fastener guide member 20, the driven fastener guide 10 may initially align the fastener 14 by engaging, e.g. screwing, the end of the fastener guide member 20 with the bone plate 16. Thereafter, the driven fastener guide 10 may simultaneously disengage the fastener guide member 20 and insert the fastener 14 within the bone plate 16. For instance, the elongated driver 30 and the collar 22 may simultaneously rotate in opposite directions in order to unscrew the fastener guide member 20 from the hole 18 which allows the bone screw 14 to pass through the fastener guide member 20 and be accordingly screwed into the hole 18. The driven fastener guide 10 may be considered a universal driver 10 since it does not require the bone plate 16 to have any additional or separate mating features other than the existing threaded through hole 18 itself.

The driven fastener guide 10 may also include a drill mount 34 that is removably connected to the drill 12 by way of a clamping mechanism. The drill mount 34 is connected to the housing 32 and thus removably connects the housing 32 to the drill 12 by way of the clamping mechanism. The drill mount 34 provides a stable and sturdy connection between the housing 32 and the drill 12. It should be appreciated that the driven fastener guide 10 may not include the drill mount 34 such that only the elongated driver 30 is operably coupled to the drill 12. In such a configuration, the user may manually hold onto the housing 32 to make the collar 22 spin in reverse. Also, the driven fastener guide 10 may be fixedly attached to the drill 12.

Figure 4:
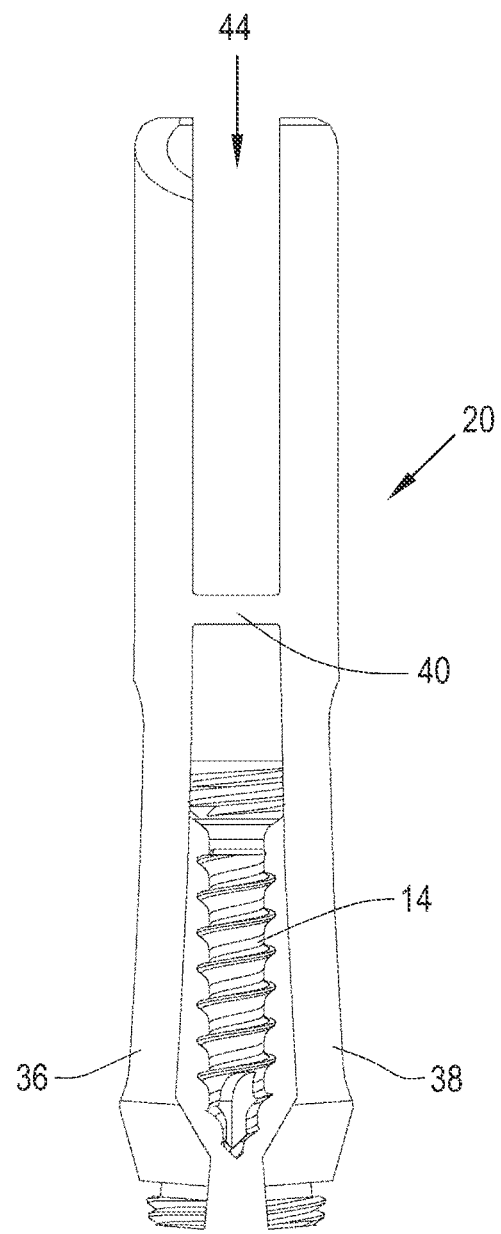
FIG. 4 is a side view of the deformable end of the screw guide driver of FIG. 1.

The fastener guide member 20 holds and guides the screw 14. The fastener guide member 20 also aligns the screw 14 by threading into, or otherwise engaging, the hole 18 of the bone plate 16. The fastener guide member 20 generally includes a split body 36, 38, 40, 42. The split body includes left and right portions 36, 38, a connecting member 40 which connects the two portions 36, 38 together, and one or more beams 42 for engaging with and temporarily holding the screw 14 within the internal cavity or through-bore 44 of the fastener guide member 20 (FIG. 4). The split body of the fastener guide member 20 includes an upper end which is engageable with the collar 22 and a lower threaded end which is engageable with the threaded hole 18 of the bone plate 16. It is noted that lower end of the split body may or may not be threaded. It should be appreciated that the fastener guide member 20 may guide the screw 14 and/or any desired tool or device. For instance, the fastener guide member 20 may be used to guide bone preparation tools, e.g. drills or taps, prior to insertion of the screw 14 into the fastener guide member 20. The fastener guide member 20 may comprise any desired material such as a deformable material, including metal and/or plastic.

The fastener guide member 20 is operably connected to the elongated driver 30 by way of the collar 22. The fastener guide member 20 may be removably attached to the collar 22. For instance, the fastener guide member 20 can be press-fit within the collar 22, coupled to the collar 22 by one or more fasteners, have one or more mating features which selectively engage with corresponding mating features of the collar 22, and/or simply be received within the collar 22 without being permanently fixed to the collar 22. Additionally, for example, protrusions 46 inside the collar 22 may engage with corresponding removal slots 48 of the fastener guide member 20 (FIG. 5).

Figure 1:
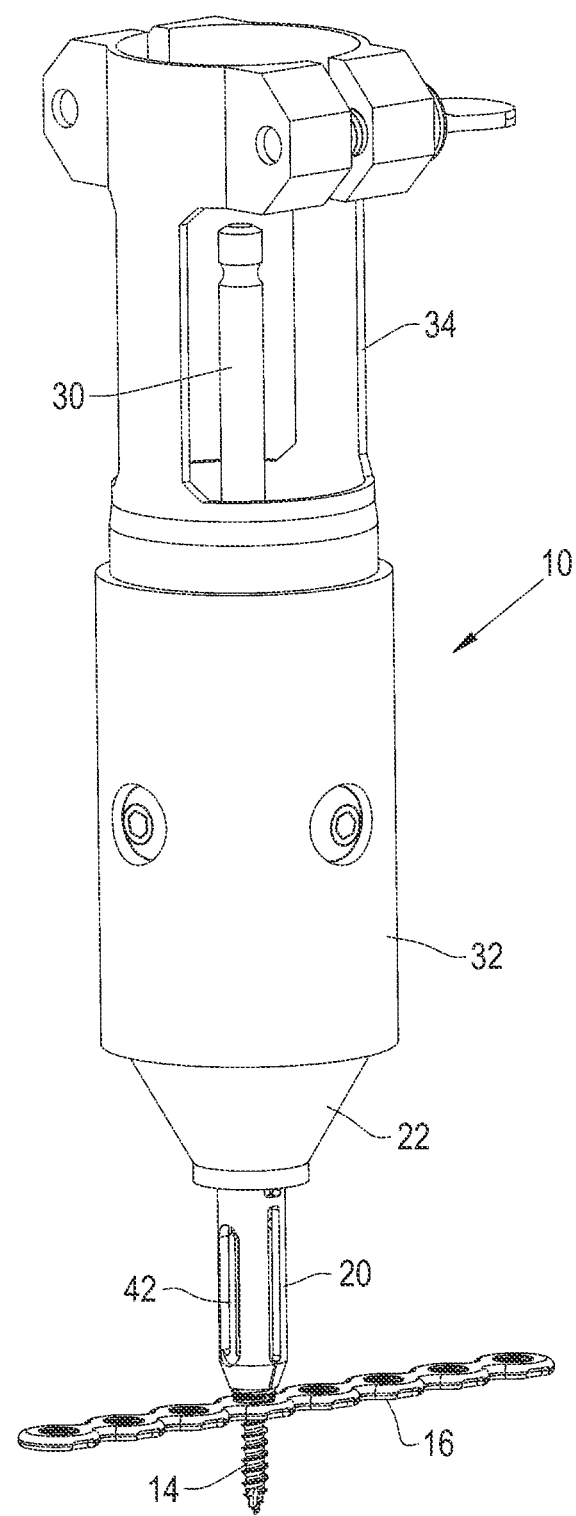
FIG. 1 is a perspective view of an embodiment of a universal screw guide driver for driving a screw into a bone plate, the screw guide driver includes a guide member, a collar, a gearing assembly, an elongated driver bit, and a housing.
Figure 2:
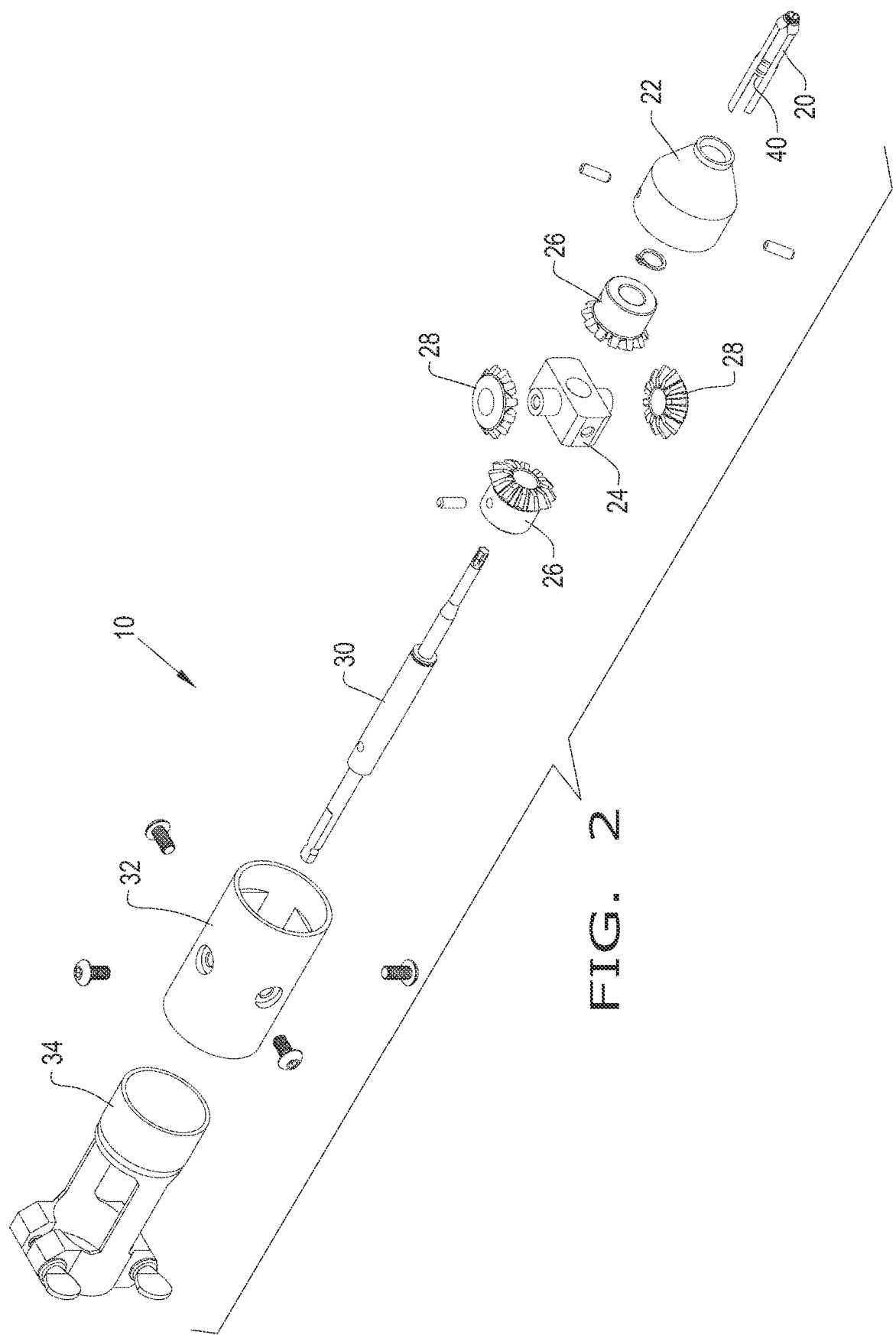
FIG. 2 is an exploded view of the screw guide of FIG. 1.

The portions 36, 38 may flex or bend relative to one another because the portions 36, 38 are only connected to one another by the connecting member 40 (FIGS. 2 and 4). In more detail, the connecting member 40 may comprise a pair of arcuate and substantially horizontal linking arms which rigidly link the portions 36, 38 together at an attachment point such that the portions 36, 38 may flex relative to the attachment point. The portions 36, 38 may be pressed or squeezed together to allow the fastener guide member 20 to be screwed into the hole 18 of the bone plate 16. Additionally, for example, the portions 36, 38 may be flexed outwardly or separated from one another. The user may manually flex the portions 36, 38 outwardly and/or upon inserting a screw 14 into the fastener guide member 20, the portions 36, 38 may automatically flex outwardly by way of the force of the screw 14 acting against the inner walls of the portions 36, 38. Hence, an opening or gap between the portions 36, 38 may widen for allowing the screw 14 to enter or exit the fastener guide member 20. In this regard, the internal walls of the portions 36, 38 may contact the screw 14 for applying a retaining force onto the screw 14 to retain the screw within the cavity 44 of the fastener guide member 20. It should be appreciated that the connecting member 40 may be in the form of a pin or hinge member which allows the portions 36, 38 to pivot relative to one another.

The one or more beams 42, i.e., retaining members, may be located on the portions 36, 38. More particularly, one or both of the portions 36, 38 may have a slot in its side with the beam 42 extending upwardly from the bottom of the slot.

Each beam 42 may extend upwardly and inwardly such that each beam 42 at least partially extends into the cavity 44 of the fastener guide member 20 to cause interference with, i.e., contact, the screw 14. Thereby, each beam 42 may help hold the screw 14 within the cavity 44 of the fastener guide member 20 by way of contacting and applying a retention force onto a side of the screw 14. Applying a downward force on the screw 14, by the elongated driver 30, will force the beam(s) 42 outwardly so that the screw 14 may pass through the fastener guide member 20. As can be appreciated, each beam 42 may be machined from a sidewall of the fastener guide member 20 such that the bottom of the beam 42 remains coupled with main body of the fastener guide member 20 and the top of the beam 42 is free to extend inwardly into the cavity 44 of the fastener guide member 20. Each beam 42 may extend at least partially, for example substantially, along the length of the fastener guide member 20. It should be appreciated that the fastener guide member 20 may not include any beams 42.

The collar 22 may be connected to the housing 32 and a gear 26 via one or more fasteners, such as pins, screws, bolts, etc. The collar 22 may also removably mount the fastener guide member 20. For instance, the collar 22 and the fastener guide member 20 may each include a corresponding mating feature, e.g. corresponding groove(s) and protrusion(s). Additionally, the collar 22 could also be fitted with a retaining feature, e.g. magnet, ball detent, etc., to retain the fastener guide member 20 and prevent unattended disassociation between the collar 22 and the fastener guide member 20. The collar 22 may also at least partially house any one of the gears 26, 28. The collar 22 may comprise any desired material such as metal and/or plastic.

The gearing assembly of the driven fastener guide 10 may generally include the gear mount 24, a pair of sun gears 26 in the form of input and output gears 26 mounted on the elongated driver 30, and a pair of intermediary, i.e., planetary gears 28 rotatably mounted onto the gear mount 24. The gear mount 24 has a center through hole for receiving the elongated driver 30 and a pair of protrusions which mount the planetary gears 28. The proximal, input gear 26 may be fixedly attached to the elongated driver 30 via one or more fasteners. The distal, output gear 26 may be coupled to the collar 22 via one or more fasteners. The rotary motion which is inputted by the elongated driver 30 is operably reversed by the gears 26, 28 so that the collar 22, and fastener guide member 20 therewith, rotate in an opposite direction to the elongated driver 30. The driven fastener guide 10 may include any number of gears. The gear ratio may be such that the fastener guide member 20 spins faster or slower than the elongated driver 30. Alternatively, the driven fastener guide 10 may include dual motors for generating the opposition rotation of the fastener guide member 20 and elongated driver 30.

The elongated driver 30 has one end for connecting to the drill 12 and an opposite end for connecting to the screw 14. The elongated driver 30 may also contact and/or mount the gear mount 24 and the gears 26, 28. The elongated driver 30 may also movably engage with the collar 22 via one or more bearings. The elongated driver 30 may be in the form of a drill bit 30. It should be appreciated that the end of the elongated driver 30 may have any desired configuration for engaging with any desired screw 14.

Figure 3:
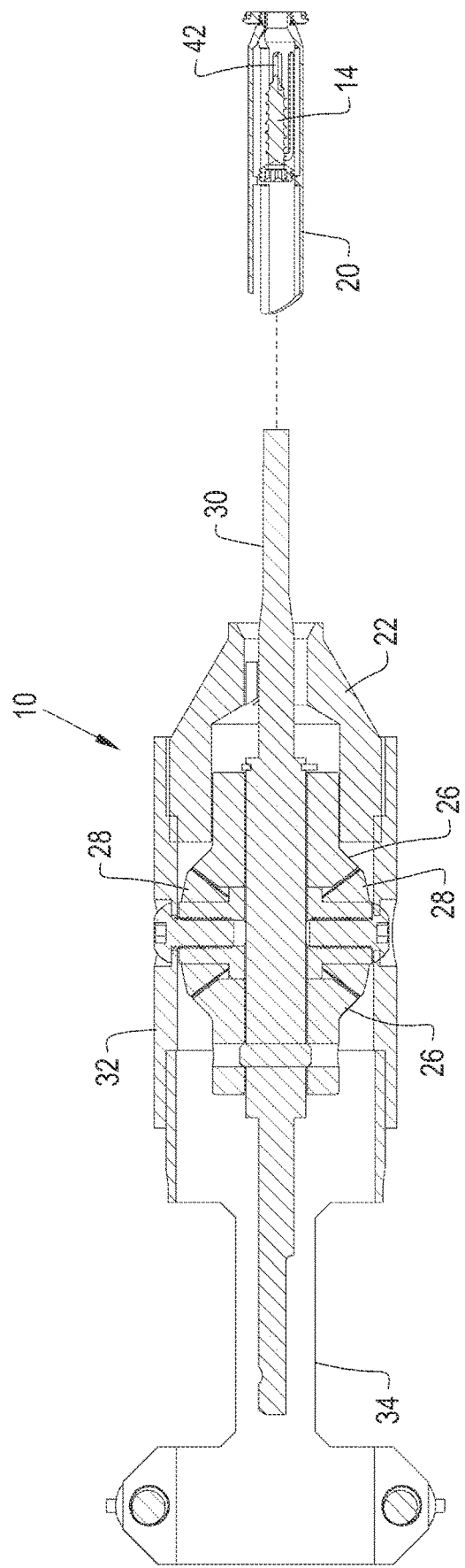
FIG. 3 is a cross-sectional view of the screw guide with the guide member being disconnected from the collar.

The housing 32 may be connected to the drill mount 34. The housing 32 may extend over at least a portion of the drill mount 34 and the collar 22, respectively (FIG. 3). The housing 32 may have a substantially tubular body with a circular cross-section. The housing 32 may also have internal grooves and/or protrusions for securing or otherwise accommodating the drill mount 34, the gears 26, 28, and/or the collar 22.

In operation, the user initially places a screw 14 inside of the fastener guide member 20. The one or more beams 42 may hold the screw 14 within the fastener guide member 20. Since the fastener guide member 20 is not attached to the driven guide 10, the user may position the fastener guide member 20 in the bone plate 16 before positioning the driven guide 10. For instance, the user may press the portions 36, 38 of fastener guide member 20 together and screw the fastener guide member 20 into the hole 18 of the bone plate 16 (FIG. 5). Additionally, the user may insert multiple fastener guide members 20 into respective holes 18 in the bone plate 16; thus, pre-aligning numerous screws 14 which are ready to be inserted into the bone via the driven guide 10. Then, the user will position the driven fastener guide 10 above a respective fastener guide member 20. The user may start drill 12 in a clockwise direction and advance the screw 14 into the bone through the hole 18 of the bone plate 16. Before the screw head seats in the bone plate 16, the collar 22 engages the fastener guide member 20 and starts to unscrew the fastener guide member 20 from the bone plate 16. In other words, prior to the screw 14 completely seating in the hole 18, protrusions 46 inside the collar 22 will engage the removal slots 48 of the fastener guide member 20 and rotate fastener guide member 20 in a counterclockwise direction and out of the hole 18 (FIG. 5). It is noted that the screw 14 applies a force onto the inner walls of the fastener guide member 20 so that the portions 36, 38 expand away from one another as the screw 14 is driven downwardly. With the fastener guide member 20 being disassociated from the hole 18, the screw 14 can be fully seated in hole 18 (FIG. 6). Hence, the fastener guide member 20 is fully removed in time to allow the screw head to pass completely through the fastener guide member 20 and into the bone plate 16. Thereby, screw alignment is advantageously maintained since the screw 14 is substantially inserted into the bone before the fastener guide member 20 is removed from the bone plate 16.

Referring now to FIGS. 8-14, there is shown a driven, multipart driven guide 50 for guiding and inserting fasteners 14 into variously configured bone plates 16 which may not have mating features for engaging with the driven guide 50. The driven guide 50 is attachable to a handheld drill 12. The driven guide 50 generally includes an outer sleeve 52, a split stem or fastener guide member 54, a flexible spacer 56 coupled to the stem 54, and a biasing member 58 connected in between the outer sleeve 52 and the stem 54. An elongated driver 60 can be inserted into and engaged with the driven guide 50 so that the stem 54 may be initially screwed into a desired hole 18 of the bone plate 16. As the elongated driver 60 drives or pushes the screw 14 downwardly toward the bone plate 16, the stem 54 will move upwardly away from the bone plate 16, and the elongated driver 60 may be subsequently driven to thread the screw 14 inside the hole 18 of the bone plate 16.

The outer sleeve 52 is movably connected to the stem 54. The outer sleeve 52 may generally include a substantially cylindrical body with an upper end and a lower end. The inside surface of the upper end may contact the upper end of the stem 54. The lower end may contact the bone plate 16. The body may also include one or more side openings and one or more inwardly extending mounting protrusions 62 for mounting and supporting the biasing member 58. Therein, the outer sleeve 52 may be movably connected to the stem 54 by way of the biasing member 58 which is connected in between corresponding protrusions 62, 64 of the outer sleeve 52 and the stem 54. The outer sleeve 52 may comprise any desired material.

Figure 13:
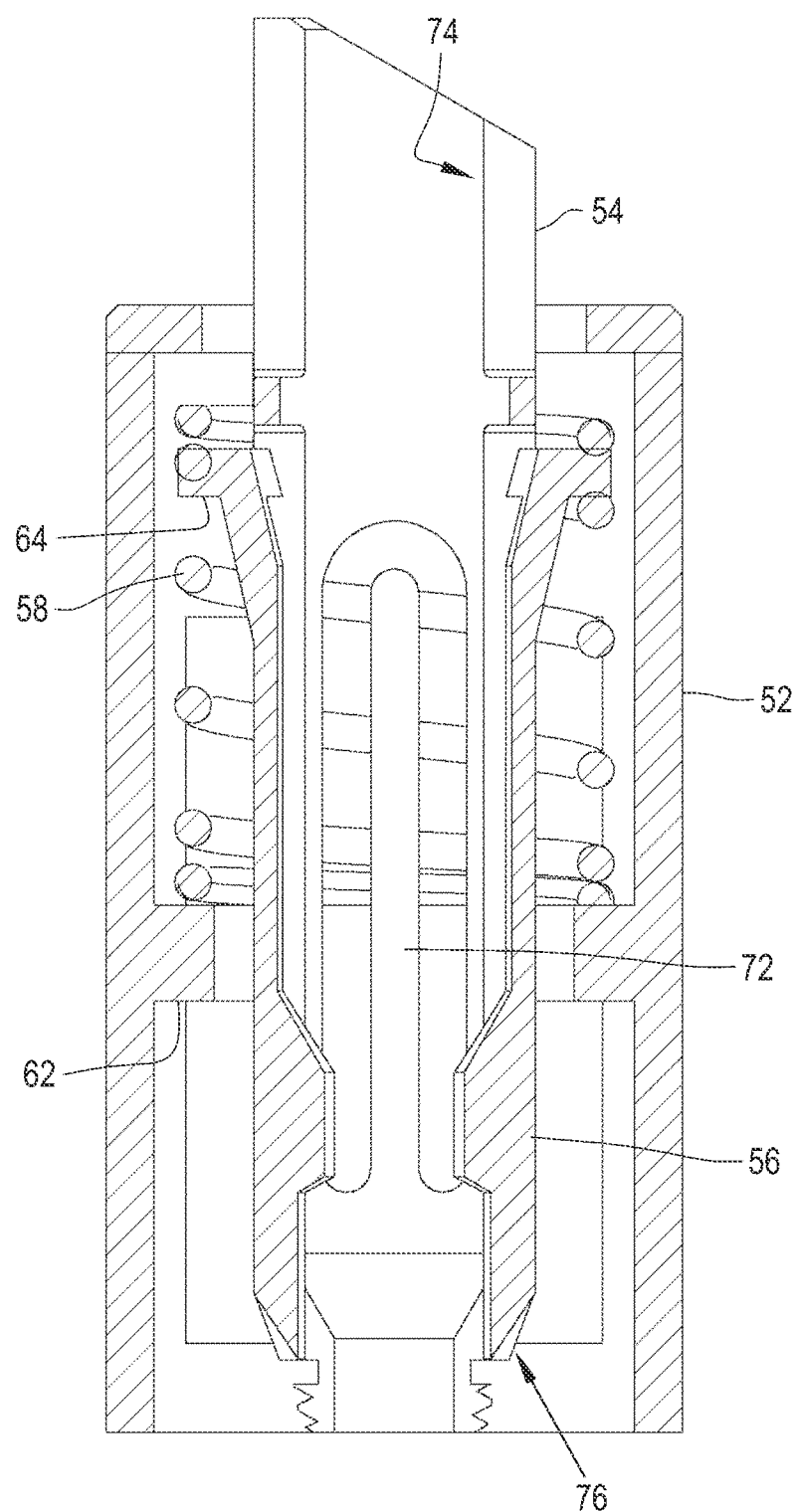
FIG. 13 is a cross-sectional view of the screw guide, taken across line 13-13 of FIG. 12.
Figure 14:
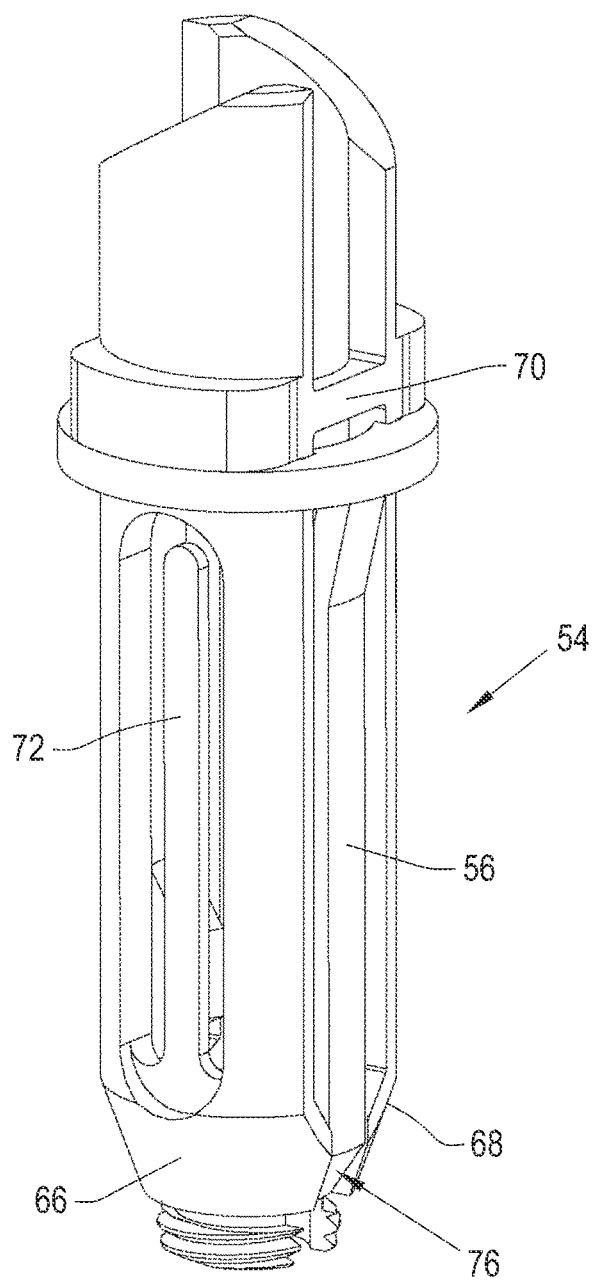
FIG. 14 is a perspective view of the split stem of the screw guide of FIGS. 8-13.

The stem 54 is operably connected to the elongated driver 60. The stem 54 is also movably connected to the outer sleeve 52. The stem 54 includes an upper end that selectively contacts the outer sleeve 52 and a lower end that is engageable with the bone plate 16. The upper end has one or more inwardly extending mounting protrusions 64 for engaging with the biasing member 58. The stem 54 includes a split body with left and right portions 66, 68, a connecting member 70 which connects the two portions 66, 68 together, and one or more beams 72 for engaging with and temporarily holding the screw 14 within the internal cavity or through-bore 74 of the stem 54 (FIGS. 13-14). The stem 54 is configured for temporarily housing the screw 14 and removably connecting to the hole 18 of the bone plate 16 so that the screw 14 may be aligned with and easily inserted into the hole 18. It should be appreciated that the stem 54 may also be used to guide bone preparation tools, e.g. drills, traps, etc. The one or more beams 72 may be designed and function similarly to the one or more beams 42, as discussed above. The stem 54 may comprise any desired material such as a deformable material, including metal and/or plastic.

The flexible spacer 56 is connected to the stem 54 and extends at least partially in between the portions 66, 68 of the stem 54 in order to prevent the portions 66, 68 from collapsing inwardly relative to one another. Meaning, in at least one location, a portion of the flexible spacer 56 extends at least partially in between the portions 66, 68 of the stem 54 to prevent the portions 66, 68 from moving inwardly toward each other. As shown, the flexible spacer 56 has a split body with two body portions that respectively fit within both of the spaces or slits in between the portions 66, 68 of the stem 54 (FIG. 14). The flexible spacer 56 is configured for temporarily preventing the portions 66, 68 from collapsing so that the threaded end of the stem 54 can be screwed into the hole 18 of the bone plate 16. The flexible spacer 56 is also configured for flexing inwardly, which thereby allows the portions 66, 68 to collapse, i.e., move inwardly toward each other, so that the threaded end of the stem 54 can be disengaged from and lifted out of the hole 18 of the bone plate 16. The flexible spacer 56 has a body which is bent inwardly for contacting the head of the screw 14. In this regard, the flexible spacer 56 has a design which allows clearance with the shank of the screw 14 but interference with the head of the screw 14. The ends of the flexible spacer 56 each have a slanted shoulder 76. The slanted shoulders 76, upon contacting the hole 18 of the bone plate 16, cause the flexible spacer 56 to flex in order to allow the portions 66, 68 of the stem 54 to collapse (FIG. 13). For instance, the flexible spacer 56 may flex outwardly in order to allow the stem 54 to accordingly collapse. The flexible spacer 56 may comprise any desired material, such as a deformable material, including metal and/or plastic.

The biasing member 58 is located in between the protrusions 62, 64 of the outer sleeve 52 and the stem 54. The biasing member 58 is configured for lifting the stem 54 upwardly relative to the outer sleeve 52. In other words, the biasing member 58 biases the stem 54 to contact the inside surface of the upper end of the outer sleeve 52. The biasing member 58 may be in the form of any desired biasing member, such as a coil spring.

Figure 8:
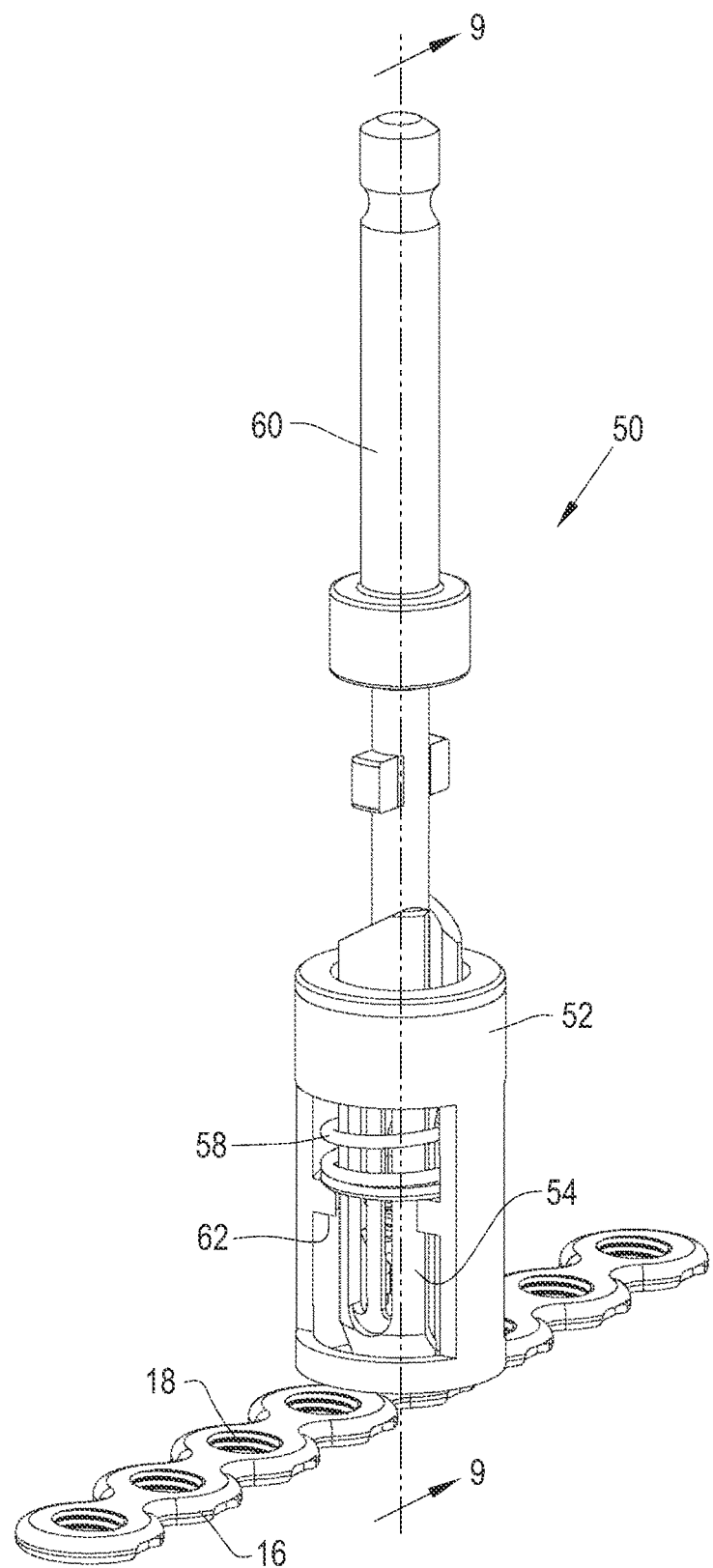
FIG. 8 is a perspective view of another embodiment of a multipart screw guide that is driven by a drill bit of a handheld drill, the screw guide includes an outer sleeve, a split stem, a flexible spacer, and a biasing member.
Figure 9:
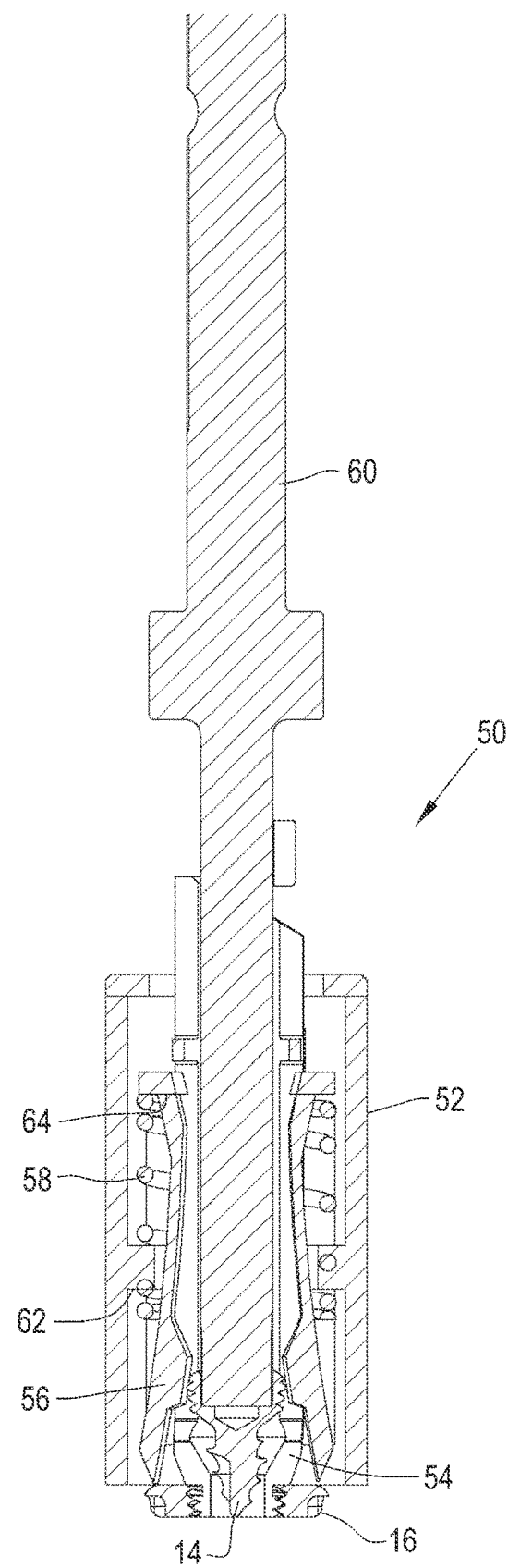
FIG. 9 is a cross-sectional view of the screw guide, taken across line 9-9 of FIG. 8.
Figure 10:
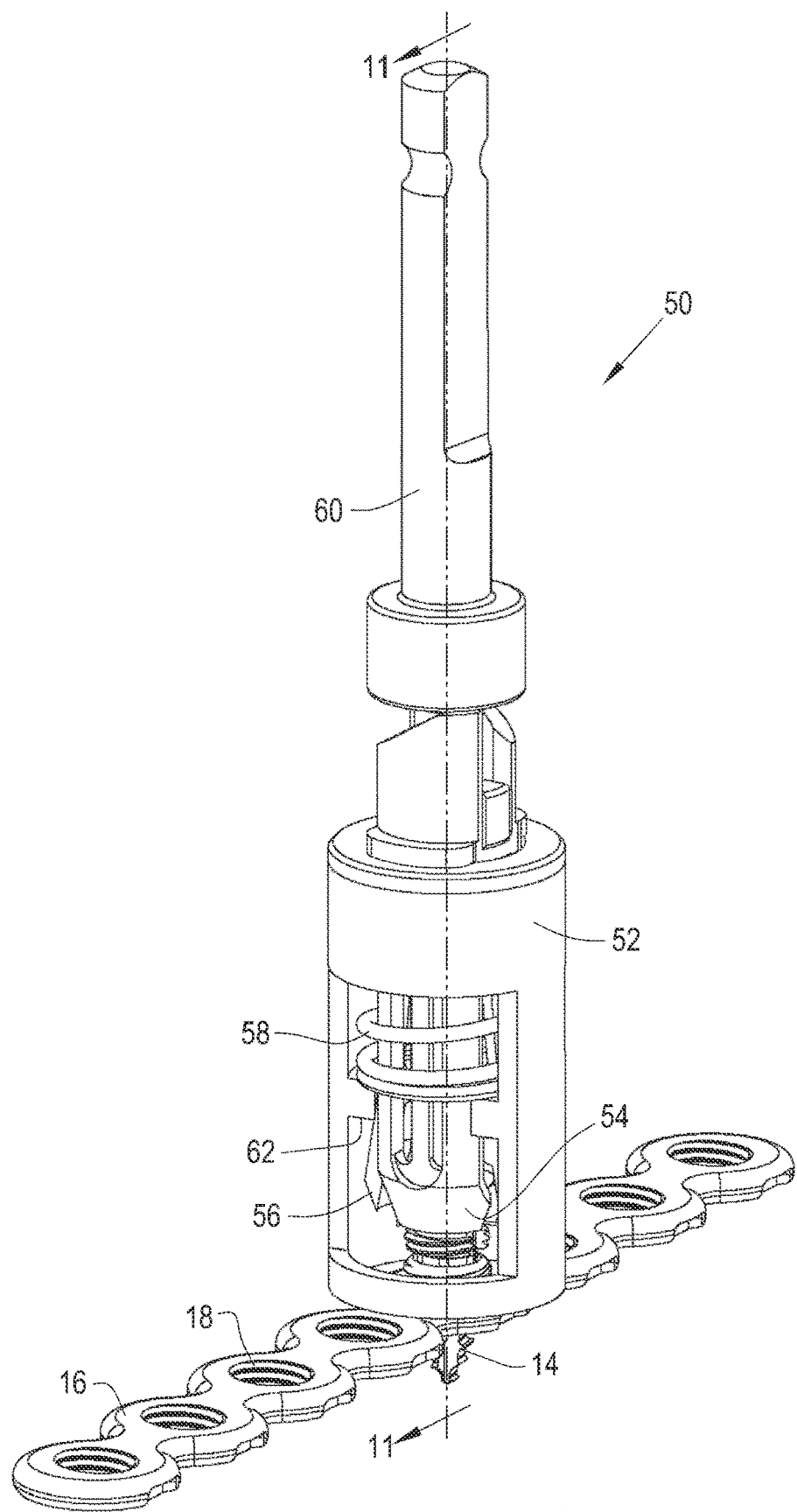
FIG. 10 is a perspective view of the screw guide, wherein the drill bit is engaged with the outer sleeve and the screw is seated within the bone plate.
Figure 11:
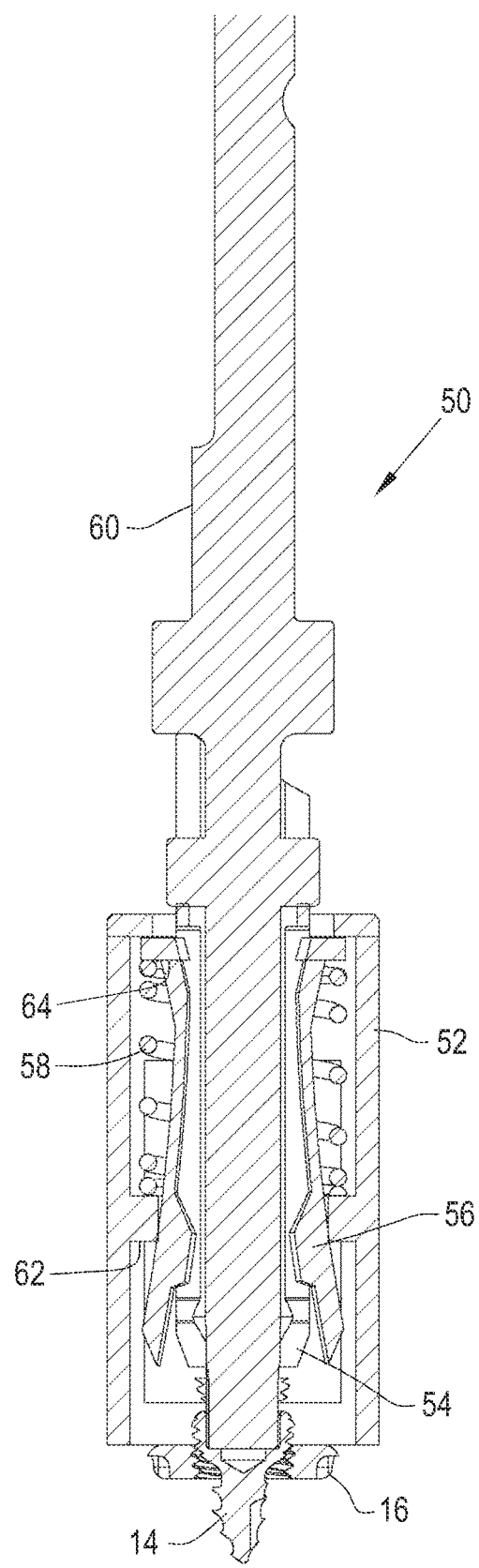
FIG. 11 is a cross-sectional view of the screw guide, taken across line 11-11 of FIG. 10.
Figure 12:
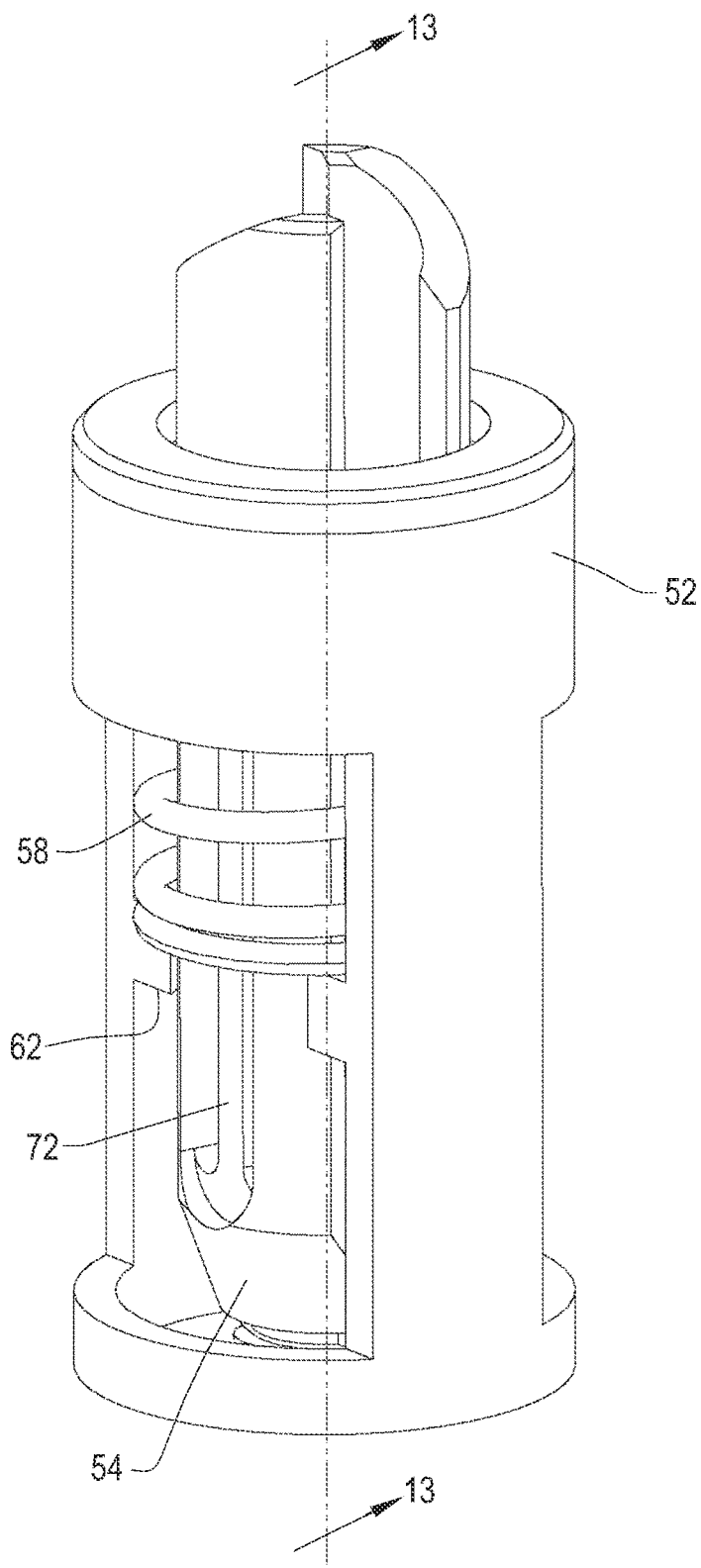
FIG. 12 is a perspective view of the screw guide of FIG. 8.

In operation, the user initially places a screw 14 inside of the stem 54. Then, the user will align the stem 54 with an empty hole 18 in the bone plate 16. The user will then push down on the stem 54 and thread the entire driven guide 50 into the bone plate 16 by way of the threaded end of the stem 54 (FIGS. 8-9). Then, the user will begin the process of screwing the screw 14 into the bone plate 16 (FIGS. 10-11). Since the flexible spacer 56 and stem 54 are split, the head of the screw 14 will flex the flexible spacer 56 outwardly as the screw 14 is advanced down the stem 54 such that the threaded end of the stem 54 is able to inwardly collapse. As the head of the screw 14 approaches the top of the bone plate 16, the bosses on the elongated driver 60 will engage the stem 54 and start turning the stem 54. The shoulder 76 of the flexible spacer 56 will dually prevent the stem 54 from advancing distally cause the threaded end of the stem 54 to collapse inwardly to disengage the stem 54 from the threads in the hole 18. Then, the biasing force of the biasing member 58 will lift the stem 54 upwardly since the stem 54 is no longer attached to the bone plate 16. With the stem 54 up and out of the way of the hole 18, the screw 14 can flex the threaded end of stem 54 outward to pass through stem 54 in order to be properly seated in the hole 18 of the bone plate 16. More particularly, the head of the screw 14 will push the portions 66, 68 and the flexible spacer 56 outwardly as the elongated driver 60 screws the screw 14 into the hole 18 of the bone plate 56.

While this invention has been described with respect to at least one embodiment, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A method of guiding a fastener into a hole in a bone plate, the method comprising:
   providing or obtaining a bone plate with a threaded distal portion of a split body of a fastener guide threaded into a hole in the bone plate such that a fastener received in a through-bore in the split body is aligned with the hole in the bone plate; and
   rotating the fastener in a first direction of rotation relative to the hole in the bone plate to advance the fastener distally through the through-bore, wherein said rotating includes a first phase of fastener rotation in which the fastener advances distally through the through-bore while the threaded distal portion of the split body remains fixed rotationally relative to the hole in the bone plate and a second phase of fastener rotation following the first phase in which the fastener continues to advance distally through the through-bore while the threaded distal portion of the split body is caused to rotate in a second direction of rotation opposite the first direction relative to the hole in the bone plate for removing the fastener guide from the bone plate.

2. The method of claim 1, wherein the fastener guide incorporates at least one retaining member for retaining the fastener in the through-bore in the split body.

3. The method of claim 2, wherein, prior to said rotating, the at least one retaining member applies a retaining force to the fastener in the through-bore, and wherein, during said rotating, the fastener overcomes the retaining force.

4. The method of claim 2, wherein the at least one retaining member extends at least partially into the through-bore.

5. The method of claim 1, wherein the threaded distal portion of the split body includes a first threaded portion separable from a second threaded portion.

6. The method of claim 1, wherein the split body comprises a first longitudinal portion and a second longitudinal portion which are connected to one another but only proximal of the threaded distal portion of the split body.

7. The method of claim 1, wherein said rotating includes rotating the fastener with an elongated driver removably engaged with a head of the fastener, the elongated driver fixedly connected to an input gear of a plurality of gears configured for being driven by the elongated driver, wherein the plurality of gears additionally includes an output gear and a pair of intermediary gears connected in between the input gear and the output gear, wherein the pair of intermediary gears are configured for reversing a direction of rotation such that the input gear can rotate in the first direction of rotation along with the elongated driver while the output gear simultaneously rotates in the second direction of rotation.

8. The method of claim 7, wherein the output gear is fixedly connected to a collar.

9. The method of claim 8, wherein, during the first phase of fastener rotation, the collar is disengaged with the fastener guide, and wherein, during the second phase of fastener rotation, the collar engages the fastener guide for rotating the fastener guide in the second direction of rotation along with the collar.

10. The method of claim 9, wherein a portion of the fastener guide is receivable in the collar.

11. A method of guiding a fastener into a hole in a bone plate, the method comprising:
providing or obtaining a bone plate with a threaded distal portion of a body of a fastener guide threaded into a hole in the bone plate such that a fastener received in a through-bore in the body is aligned with the hole in the bone plate, the threaded distal portion of the body being split so as to include at least a first threaded portion that is separable from a second threaded portion; and
rotating the fastener in a first direction of rotation relative to the hole in the bone plate to advance the fastener distally through the through-bore, wherein said rotating includes a first phase of fastener rotation in which the fastener advances distally through the through-bore while the threaded distal portion of the body remains threaded into the hole in the bone plate and a second phase of fastener rotation following the first phase in which the fastener continues to advance distally through the through-bore while the threaded distal portion of the body is caused to disengage from the hole in the bone plate.

12. The method of claim 11, wherein the second phase of fastener rotation includes the threaded distal portion of the body rotating in a second direction of rotation relative to the hole in the bone plate, the second direction opposite the first direction.

13. The method of claim 11, wherein the second phase of fastener rotation includes the first threaded portion and the second threaded portion collapsing inwardly from an inner threaded wall of the hole in the bone plate.

14. A method of guiding a fastener into a hole in a bone plate, the method comprising:
providing or obtaining a bone plate with a distal portion of a body of a fastener guide removably coupled to a hole in the bone plate such that a fastener received in a through-bore in the body is aligned with the hole in the bone plate, the distal portion of the body being split so as to include at least a first end portion that is separable from a second end portion; and
rotating the fastener in a first direction of rotation relative to the hole in the bone plate to advance the fastener distally through the through-bore, wherein said rotating includes a first phase of fastener rotation in which the fastener advances distally through the through-bore while the first end portion and the second end portion maintain positioning relative to one another and a second phase of fastener rotation following the first phase in which the fastener continues to advance distally through the through-bore while the first end portion and the second end portion are caused to collapse inwardly toward one another.

15. The method of claim 14, wherein the first end portion and the second end portion each include a threaded portion, and wherein the distal portion of the body of the fastener guide being removably coupled to the hole in the bone plate includes the first end portion and the second end portion being threaded into the hole in the bone plate.

16. The method of claim 14, wherein the fastener guide incorporates at least one retaining member, and wherein, prior to said rotating, the at least one retaining member applies a retaining force to the fastener in the through-bore in the body for retaining the fastener in the through-bore.

17. The method of claim 14, wherein the fastener guide incorporates a flexible spacer that, during the first phase of fastener rotation, prevents the first end portion and the second end portion from collapsing inwardly toward one another.

18. The method of claim 17, wherein, during the second phase of fastener rotation, interference between a head of the fastener and the flexible spacer moves the flexible spacer out from between the first end portion and the second end portion to allow the first end portion and the second end portion to collapse inwardly toward one another.

19. The method of claim 17, wherein the flexible spacer includes a first distal end and a second distal end that each include a slanted distal shoulder that is slanted relative to a top surface of the bone plate.

20. The method of claim 17, wherein the fastener guide incorporates an outer sleeve and a biasing member, the outer sleeve surrounding and being movably connected to the body of the fastener guide and being configured for contacting the bone plate, the biasing member situated in between the outer sleeve and the body of the fastener guide, the biasing member surrounding the body and being configured for biasing the body to contact the outer sleeve.

* * * * *